United States Patent [19]

Dukes

[11] Patent Number: 5,020,356

[45] Date of Patent: Jun. 4, 1991

[54] METHOD AND APPARATUS FOR MEASURING CHARACTERISTICS OF A MULTILAYER PRODUCT

[75] Inventor: John R. Dukes, Worthington, Ohio

[73] Assignee: Process Automation Business, Inc., Columbus, Ohio

[21] Appl. No.: 398,757

[22] Filed: Aug. 25, 1989

[51] Int. Cl.$^5$ .................... G01G 23/01; G01G 9/00; G01G 11/04

[52] U.S. Cl. ........................................ 73/1 B; 73/865; 73/150 R; 73/159; 364/568; 364/571.05

[58] Field of Search .................. 73/1 B, 1 R, 1 J, 865, 73/866, 865.8, 159, 150 R; 364/568, 571.01–571.08; 177/50, 25.11–25.19

[56] References Cited

U.S. PATENT DOCUMENTS

| | | | |
|---|---|---|---|
| 3,564,224 | 2/1971 | Chope | 364/568 X |
| 3,579,271 | 5/1971 | Pomerontz | 73/150 R X |
| 3,596,071 | 7/1971 | Doering | 364/567 X |
| 3,650,891 | 3/1972 | Dahlin | 364/571.05 X |
| 3,668,398 | 6/1972 | Doering . | |
| 3,711,688 | 1/1973 | Stout et al. | 364/568 X |
| 3,757,122 | 9/1973 | Bosson et al. . | |
| 3,845,287 | 10/1974 | Fremont et al. | 364/568 X |
| 3,857,023 | 12/1974 | McCall | 364/568 X |
| 3,860,168 | 1/1975 | Byrd et al. | 364/568 X |
| 4,594,880 | 6/1986 | Murdoch et al. | 73/32 R |
| 4,866,984 | 9/1989 | Houghton | 73/159 |
| 4,936,141 | 6/1990 | Anderson, Jr. et al. | 356/430 X |
| 4,957,770 | 9/1990 | Howarth | 73/159 X |

FOREIGN PATENT DOCUMENTS

| | | | |
|---|---|---|---|
| 2058426 | 5/1972 | Fed. Rep. of Germany | 73/150 R |
| 2631365 | 1/1978 | Fed. Rep. of Germany | 73/150 R |
| 146492 | 2/1981 | Fed. Rep. of Germany | 73/150 R |
| 2,114,732 | 8/1983 | United Kingdom | |
| 170831 | 7/1989 | Japan | 73/866 |

OTHER PUBLICATIONS

Instrument Practice, Vol. 20, June 1966, A. Kosmowski et al, "Gauging and Controlling of Basis Weight and Thickness Using Radiomudides", pp. 512–516

Patent Abstracts of Japan, Vol. 10, No. 7 (p. 419) (2064), Jan. 11, 1986 and JP, A, 60164202 (Sumitomo Kinzoku Kogyo K.K.) Aug. 27, 1985, (Utaron Taira)

Primary Examiner—Tom Noland
Attorney, Agent, or Firm—Killworth, Gottman, Hagan & Schaeff

[57] ABSTRACT

A method and apparatus are disclosed wherein a plurality of basis weight sensors are interleaved with one or more processing stations used to conjoin or apply one or more layers to a base substrate to form a multilayer product such that a sensor is located on the input and output sides of each processing station. Each of the sensors can be calibrated with a plurality of product calibrations such that multiple output signals corresponding to multiple products can be generated simultaneously by the sensors. Each of the sensors is calibrated with product calibrations corresponding to the product or intermediate stage of the product which it monitors, the layer applied by the processing station preceding it, if any, and the layer applied by the processing station succeeding it, if any. Signals generated by the sensors may then be used directly to determine the basis weight of the resulting product and/or each intermediate stage of the product, or the signals may be processed to determine the basis weight of each layer of material of the resulting product independent of the substrate to which the layer was applied. Substrate independent layer measurement is performed by subtracting the output signal generated by the sensor preceding the processing station applying the layer based on the product calibration corresponding to the layer from the output signal generated by the sensor succeeding the processing station applying the layer based on the product calibration corresponding to the layer.

15 Claims, 3 Drawing Sheets

$\mu = f(pt) = f(\ln I/I_0)$ $\mu = \mu_0 + \mu_1 \ln I/I_0 + \mu_2 (\ln I/I_0)^2 + \cdots$

METHOD AND APPARATUS FOR MEASURING CHARACTERISTICS OF A MULTILAYER PRODUCT

BACKGROUND OF THE INVENTION

The present invention relates generally to the monitoring of industrial processes and, more particularly, to a method and apparatus for monitoring and/or controlling a process for producing a multilayer product including a base substrate and at least one layer of material deposited, coated or otherwise applied to the base substrate as it passes through a number of processing stations corresponding at least to the number of layers. While the present invention is generally applicable to monitoring and/or controlling the production of multilayer products which are produced by conjoining or applying layers to a base substrate regardless of the method of production, it will be described with reference to a coating processes to which the invention has been successfully applied.

A common way to measure and control the weight or thickness of a material coated on a substrate in an industrial manufacturing process is to measure the process before and after a coating station which applies the coating or layer to the substrate. The measurement taken before the coating station is subtracted from the measurement taken after the coating station to obtain the coating weight. Typically, the coating and the substrate are different materials and the calibration for the measuring or gauging instruments employed will be different for the two materials. The calibration of the gauging instrument succeeding the coating station in fact is dependent on the actual ratio of the coating weight to the substrate weight such that a measurement "catch 22" occurs in that the coating weight to be measured is required to be known to calibrate the gauging instrument used to measure it. Calibration of the gauging instruments is further complicated when the composition of the substrate varies within or between runs. Such substrate variation is becoming more common due to the increasing use of recycled materials such as paper in substrates and industrial applications which require deposition of the same coating materials onto many different substrates.

Accordingly there is a need for measuring and/or controlling a process for producing a multilayer product including a base substrate and at least one layer of material conjoined, deposited, coated or otherwise applied to the base substrate which simplifies calibration of measuring or gauging instruments. Preferably, the improved method and apparatus would permit measurement and/or control of the weight or thickness of each of one or more layers independently of the base substrate to which the layers are conjoined or applied yet permit measurement of the base substrate and intermediate stages of the multilayer product including the substrate and one or more intermediate layers if desired.

SUMMARY OF THE INVENTION

This need is met by the method and apparatus of the present invention wherein a plurality of measuring or gauging instruments are interleaved with one or more processing stations used to conjoin or apply one or more layers to a base substrate to form a multilayer product such that a gauging instrument is located on the input and output sides of each processing station. Each of the gauging instruments can be calibrated with a plurality of product calibrations such that multiple output signals corresponding to multiple products can be generated simultaneously by the instruments. Each of the gauging instruments is calibrated with product calibrations corresponding to the product or intermediate stage of the product which is monitored by the instrument, the product calibration for the layer applied by the processing station preceding the instrument, if any, and the product calibration for the layer applied by the processing station succeeding the instrument, if any. The signals generated by the gauging instruments are then directly used to determine the weight per unit area of material or basis weight of the resulting product and/or each intermediate stage of the product, or the signals are processed to determine the basis weight of each layer of material of the resulting product by subtracting the output signal generated by the gauging instrument preceding the processing station applying the layer based on the product calibration corresponding to the layer from the output signal generated by the gauging instrument succeeding the processing station applying the layer based on the product calibration corresponding to the layer. Thus, in applications where the substrate is a given quantity, i. e. the weight or thickness of the substrate or base material is not important but measurement and/or control of the basis weight of a layer is very important, the basis weight of the layer can be determined independently of the substrate or intermediate stage of the ultimate product to which the layer is conjoined or applied for measurement and/or control of each layer. Further, the product and each of its intermediate stages can be measured and/or controlled.

In accordance with one aspect of the present invention, a method for measuring characteristics of a product including a substrate and at least one layer of material deposited, coated or otherwise applied to the substrate as the substrate passes through a number of processing stations corresponding to at least the number of layers to be measured comprises the steps of: positioning a first gauging system on the input side of a first processing station to monitor a base substrate prior to entering the first processing station; positioning a second gauging system on the output side of the first processing station to monitor the base substrate and a first layer applied by the first processing station; calibrating the first and second gauging systems with a product calibration corresponding to the first layer; and, determining the basis weight of the first coating by subtracting a first output signal generated by the first gauging system from a second output signal generated by the second gauging system. The method may further provide for controlling at least one of the characteristics by generating a process control signal from the determined basis weight of the first layer to control the first processing station.

The basis weight of the substrate can also be determined by taking a ratio of a product calibration corresponding to the substrate to the product calibration corresponding to the first layer and multiplying the first output signal by the ratio. If more than one layer is applied to the base substrate, the method may further comprise the steps of: positioning a third gauging system on the output side of a second processing station to monitor the base substrate, the first layer applied by the first processing station and a second layer applied by the second processing station; calibrating the second and third gauging systems with a product calibration corresponding to the second layer; and, determining the basis weight of the second layer by subtracting a third output signal generated by the second gauging system and corresponding to the product calibration for the second layer from a fourth output signal generated by the third gauging system. The basis weight of the combination of the base substrate and the first layer can also be determined by taking a ratio of a product calibration corresponding to the combination of the base substrate and the first layer to the product calibration corresponding to the second layer and multiplying the third output signal by the ratio.

In accordance with another aspect of the present invention, a method for measuring characteristics of a product including a substrate and at least one layer of material deposited, coated or otherwise applied to the substrate as the substrate passes through a number of processing stations corresponding to at least the number of layers to be measured comprises the steps of: positioning a first gauging system on the input side of a first processing station to monitor a base substrate prior to entering the first processing station, the first gauging system including calibration means for defining a plurality of product calibrations each corresponding to one material or a combination of materials to be monitored, such as the base substrate and one or more layers applied thereto; positioning a second gauging system on the output side of the first processing station to monitor the base substrate and a first layer applied by the first processing station, the second gauging system including calibration means for defining a plurality of product calibrations each corresponding to one material or a combination of materials to be monitored, such as the base substrate and one or more layers applied thereto; calibrating the first gauging system with product calibrations corresponding to the base substrate and the first layer; calibrating the second gauging system with product calibrations corresponding to the first layer and to the combination of the base substrate and the first layer; determining the basis weight of the base substrate from an output signal generated by the first gauging system based on the product calibration corresponding to the base substrate; determining the basis weight of the first coating by subtracting an output signal generated by the first gauging system based on the product calibration corresponding to the first layer from an output signal generated by the second gauging system based on the product calibration corresponding to the first layer; and, determining the basis weight of the combination of the base substrate and the first layer from an output signal generated by the second gauging system based on the product calibration corresponding to the combination of the base substrate and the first layer.

For measuring a second layer, the method may further comprise the steps of: positioning a third gauging system on the output side of a second processing station to monitor the combination of the base substrate, the first layer and a second layer applied to the combination of the base substrate and the first layer by the second processing station, the third gauging system including calibration means for defining a plurality of product calibrations each corresponding to one material or a combination of materials to be monitored, such as the base substrate and one or more layers applied thereto; further calibrating the second gauging system with a product calibration corresponding to the second layer; calibrating the third gauging system with product calibrations corresponding to the second layer and to the combination of the base substrate and the first and second layers; determining the basis weight of the second coating by subtracting an output signal generated by the second gauging system based on the product calibration corresponding to the second layer from an output signal generated by the third gauging system based on the product calibration corresponding to the second layer; and, determining the basis weight of the combination of the base substrate and the first and second layers from an output signal generated by the third gauging system based on the product calibration corresponding to the combination of the base substrate and the first and second layers.

In accordance with a more general aspect of the present invention, a method for measuring characteristics of a product resulting from an industrial process wherein a base substrate passes through a number of processing stations for depositing, coating or otherwise applying one or more layers of material to the base substrate wherein gauging systems are positioned on input and output sides of the processing stations and include calibration means for defining a plurality of product calibrations each corresponding to one material or a combination of materials to be monitored, such as the base substrate and one or more layers applied thereto, and intermediate stages of the resulting product comprises the steps of: calibrating each of the gauging systems with product calibrations corresponding to the product or intermediate product monitored by the gauging system, the layer applied by the processing station preceding the gauging system, if any, and the layer applied by the processing station succeeding the gauging system, if any; determining the basis weight of the resulting product and each intermediate stage of the resulting product from output signals generated by the corresponding gauging systems based on the product calibrations corresponding to the resulting product and each intermediate stage of the resulting product; and, determining the basis weight of each layer of material of the resulting product by subtracting an output signal generated by the gauging system preceding the processing station applying the layer based on the product calibration corresponding to the layer from an output signal generated by the gauging system succeeding the processing station applying the layer based on the product calibration corresponding to the layer.

In accordance with still another aspect of the present invention, a system for measuring characteristics of a product including a substrate and at least one layer of material deposited, coated or otherwise applied to the substrate as the substrate passes through a number of processing stations corresponding to at least the number of layers to be measured comprises first gauging means positioned on the input side of a first processing station for monitoring a base substrate prior to entering the first processing station and generating a first output signal representative of the base substrate. Second gauging means are positioned on the output side of the first processing station for monitoring the base substrate and a first layer applied by the first processing station and generating a second output signal representative of the substrate and the first layer. The first and second gauging means are calibrated with a product calibration corresponding to the first layer. Calculating means provide for determining the basis weight of the first coating by subtracting the first output signal generated by the first gauging system from the second output signal generated by the second gauging system. The system may further comprise process control means for controlling at least one of the characteristics by generating a process control signal from the determined basis weight of the first layer to control the first processing station.

The control means may further provide for taking a ratio of a product calibration corresponding to the substrate to the product calibration corresponding to the first layer and determining the basis weight of the base substrate by multiplying the first output signal by the ratio. The system may further comprise third gauging means positioned on the output side of a second processing station for monitoring the combination of the base substrate, the first layer applied by the first processing station and a second layer applied by the second processing station, the second and third gauging means being calibrated with a product calibration corresponding to the second layer. The calculating means then further provides for determining the basis weight of the second layer by subtracting a third output signal generated by the second gauging system and corresponding to the product calibration for the second layer from a fourth output signal generated by the third gauging system.

In accordance with yet another aspect of the present invention, a system for measuring characteristics of a product including a substrate and at least one layer of material deposited, coated or otherwise applied to the substrate as the substrate passes through a number of processing stations corresponding to at least the number of layers to be measured comprises first gauging means positioned on the input side of a first processing station for monitoring a base substrate prior to entering the first processing station, the first gauging means including calibration means for defining a plurality of product calibrations each corresponding to one material or a combination of materials to be monitored, such as the base substrate and one or more layers applied thereto, the first gauging means being calibrated with product calibrations corresponding to the base substrate and the first layer. Second gauging means are positioned on the output side of the first processing station for monitoring the base substrate and a first layer applied by the first processing station, the second gauging means including calibration means for defining a plurality of product calibrations each corresponding to one material or a combination of materials to be monitored, such as the base substrate and one or more layers applied thereto, the second gauging means being calibrated with product calibrations corresponding to the first layer and to the combination of the base substrate and the first layer. Calculating means are provided for determining the basis weight of the base substrate from an output signal generated by the first gauging system based on the product calibration corresponding to the base substrate, the basis weight of the first coating by subtracting an output signal generated by the first gauging system based on the product calibration corresponding to the first layer from an output signal generated by the second gauging system based on the product calibration corresponding to the first layer, and the basis weight of the combination of the base substrate and the first layer from an output signal generated by the second gauging system based on the product calibration corresponding to the combination of the base substrate and the first layer.

In accordance with a more general apparatus aspect of the present invention, a system for measuring characteristics of a product including a base substrate and at least one layer of material deposited, coated or otherwise applied to the base substrate as it passes through a number of processing stations corresponding to at least the number of layers to be measured comprises a plurality of gauging means positioned on input and output sides of the processing stations each including calibration means for defining a plurality of product calibrations each corresponding to one material or a combination of materials to be monitored, such as the base substrate and one or more layers applied thereto, the plurality of gauging means each being calibrated with product calibrations corresponding to the product or intermediate stage of the product monitored by the gauging system, the layer applied by the processing station preceding the gauging means, if any, and the layer applied by the processing station succeeding the gauging system, if any. Calculating means are provided for determining the basis weight of the resulting product and/or one or more intermediate stages of the resulting product from output signals generated by the corresponding gauging means based on the product calibrations corresponding to the resulting product and each intermediate stage of the resulting product, and determining the basis weight of each layer of material of the resulting product by subtracting an output signal generated by the gauging system preceding the processing station applying the layer based on the product calibration corresponding to the layer from an output signal generated by the gauging system succeeding the processing station applying the layer based on the product calibration corresponding to the layer.

It is an object of the present invention to provide an improved method and apparatus for measuring and/or controlling a process for producing a multilayer product including a base substrate and at least one layer of material conjoined, deposited, coated or otherwise applied to the base substrate which simplifies calibration of measuring or gauging instruments; to provide an improved method and apparatus for measuring and/or controlling a process for producing a multilayer product including a base substrate and at least one layer of material conjoined, deposited, coated or otherwise applied to the base substrate wherein gauging systems positioned intermediate processing stations which apply layers to the base substrate are calibrated to directly monitor the product or intermediate stage of the product passing by each gauging system and, in conjunction with gauging systems on the other side of adjacent processing stations, to determine the basis weight of layers applied by those processing stations; and, to provide an improved method and apparatus for measuring and/or controlling a process for producing a multilayer product including a base substrate and at least one layer of material conjoined, deposited, coated or otherwise applied to the base substrate wherein layers can be monitored independently of the substrate to which the layers are applied whether the substrate is a base substrate or a combination of a base substrate and one or more layers applied to the base substrate.

Other objects and advantages of the invention will be apparent from the following description, the accompanying drawings and the appended claims.

BRIEF DESCRIPTION OF THE INVENTION

DETAILED DESCRIPTION OF THE INVENTION

Figure 1:
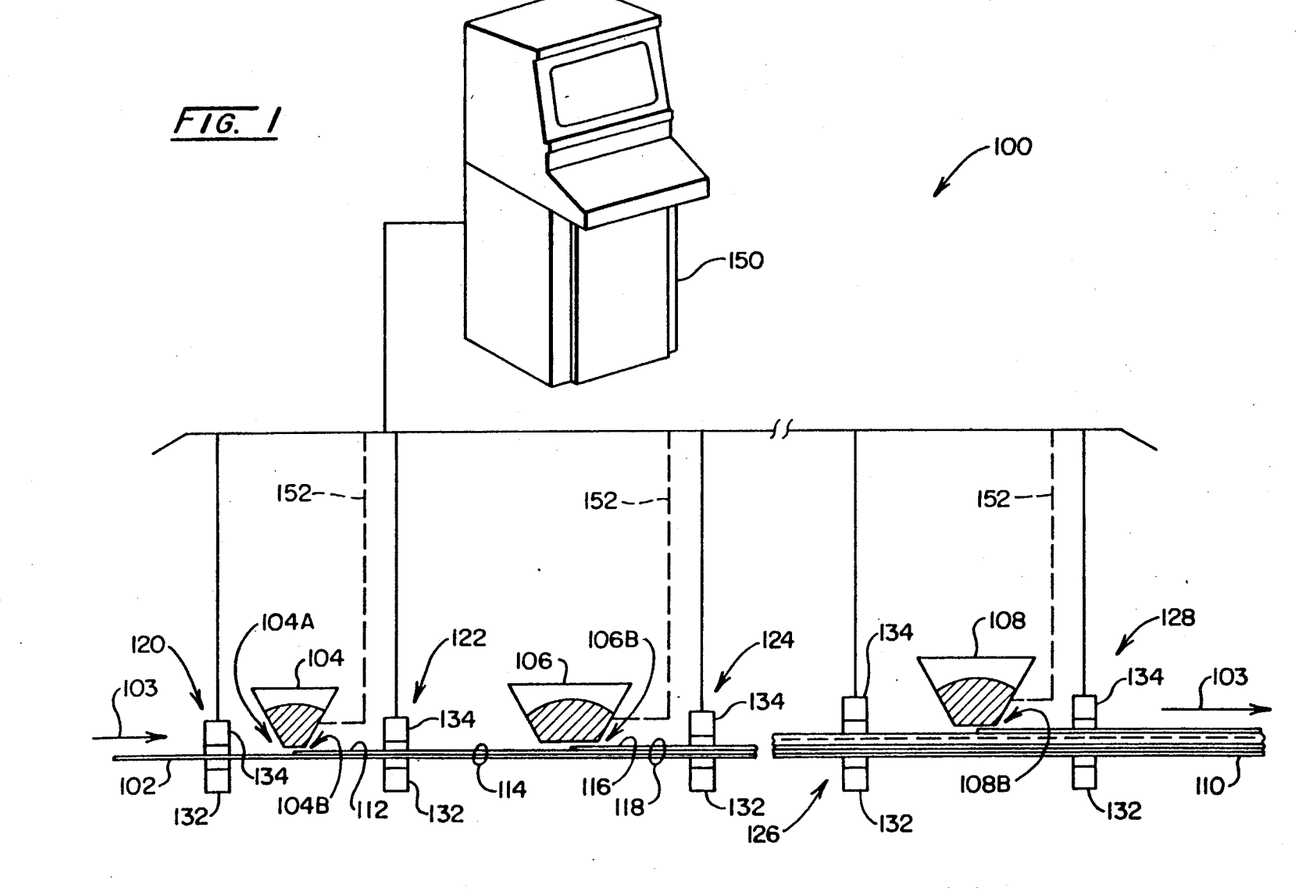
FIG. 1 is a schematic illustration of a coating process system operable in accordance with the present invention for applying, measuring and controlling layers of material applied to a base substrate.

FIG. 1 is a schematic illustration of an industrial system 100 for performing a coating process wherein a number of layers of material are applied to a base substrate 102 as the substrate 102 travels through a number of processing or coating stations in the direction of the arrows 103. Three coating stations 104, 106 and 108 are shown in FIG. 1; however, any reasonable number of stations can be provided to coat the substrate 102 with one or more coatings as required to form a multilayer product 110 which emerges from the output side 108B of the last coating station 108 of the system 100 as indicated by the break in the drawing between coating stations 106 and 108.

One example of such an industrial coating system is a sandpaper manufacturing system wherein the base substrate 102 is paper, cloth or the like to which an adhesive layer 112 is applied by the first coating station 104 to form an intermediate product 114 made up of the base substrate 102 and the first or adhesive layer 112. The intermediate product 114 passes through the second coating station 106 which adds a second or grit layer 116 thereto to form the final multilayer product 118, i.e. sandpaper comprising the substrate 102 (paper, cloth or the like) coated with adhesive and grit layers 112, 116, respectively. In the manufacture of sandpaper, there are thousands of base-adhesive-grit combinations and accurate layer or coat weight control is more important than accurate base material weight determination or determination of the basis weight of the substrate 102.

A common way to measure and control the weight or thickness of a material coated on a substrate in an industrial manufacturing process such as the adhesive and grit layers 112, 116 for sandpaper is to measure the process before and after a coating station which applies the coating or layer to the substrate. To this end, a number of gauging means or basis weight ($B_w$) sensors 120, 122, 124, 126 and 128 are provided. First gauging means comprising a first basis weight sensor 120 is positioned on the input side 104A of the first coating station 104 for monitoring the base substrate 102 prior to entering the first coating station 104 and generating a first output signal representative of the base substrate 102. Second gauging means comprising a second basis weight sensor 122 is positioned on the output side 104B of the first coating station 104 for monitoring the base substrate 102 and the first or adhesive layer 112 applied by the first coating station 104 and generating a second output signal representative of the combination of the substrate 102 and the adhesive layer 112.

To attempt to obtain the basis weight of the first adhesive coating 112, the measurement taken before the first coating station 104 is subtracted from the measurement taken after the coating station 104. Unfortunately, the first adhesive coating 112 and the base substrate 102 are different materials such that the first and second basis weight sensors 120, 122 have to be calibrated differently to accurately measure the two materials. Accordingly, simply subtracting measurement signals from the first and second basis weight sensors 120, 122 will result in an erroneous result. This problem is overcome in accordance with the present invention such that layers conjoined, coated, deposited or otherwise applied to a base substrate can be accurately measured independently of the substrate to which the coating is applied and also, if desired, the substrate whether it is the base substrate, the finished product with all coatings/layers or an intermediate product comprising a substrate with one or more layers applied to a base substrate can be measured and/or controlled.

A wide variety of sensors are commercially available for measuring the basis weight of a sheet of material. Basis weight is the weight per unit area of the sheet which is calculated by multiplying the sheet density (p) times its thickness (t). Available sensors measure the basis weight by directing radiation at one side of a sheet and measuring the radiation which is transmitted through the sheet. Radiation used in sensors can be that associated with electromagnetic radiation such as light, x-rays and other wavelengths or particulate radiation such as beta and other nuclear particles. The present invention will be described relative to a nuclear radiation sensor which is commercially available from the assignee of the present application; however, it is to be understood that it is generally applicable to other sensors used to measure basis weight of a sheet of material.

Figure 2:
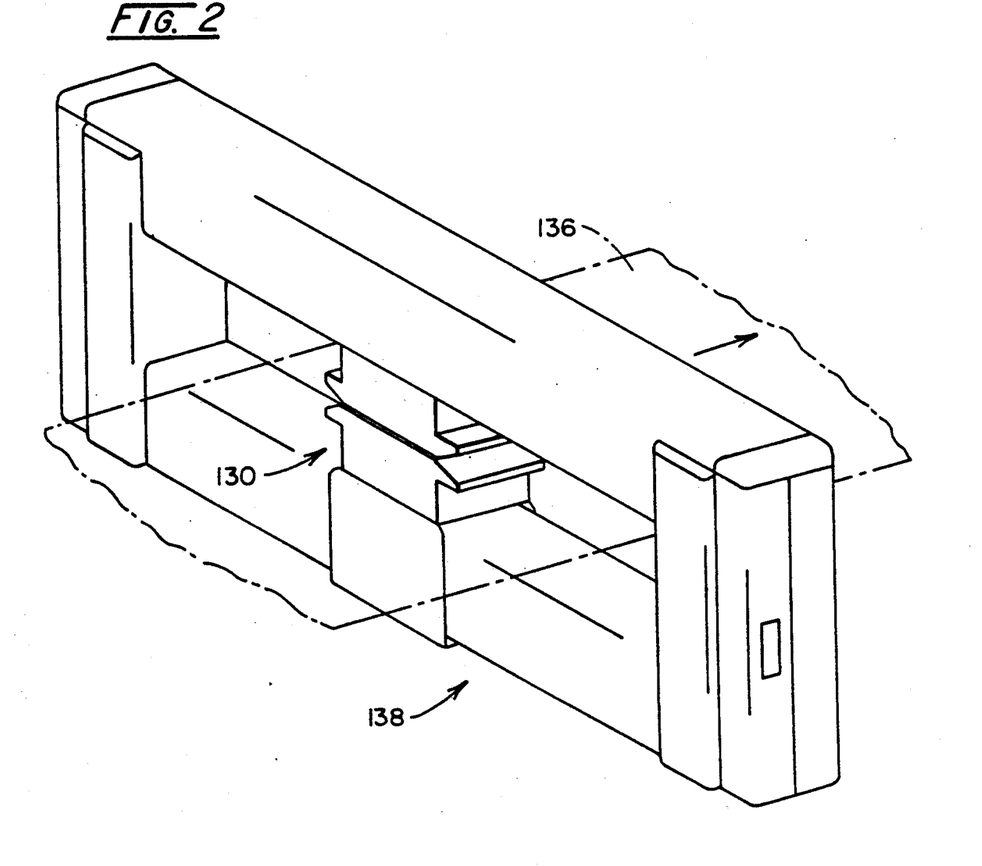
FIG. 2 is a perspective view of a measuring or gauging system scanning frame or platform for use in the present invention.
Figure 3:
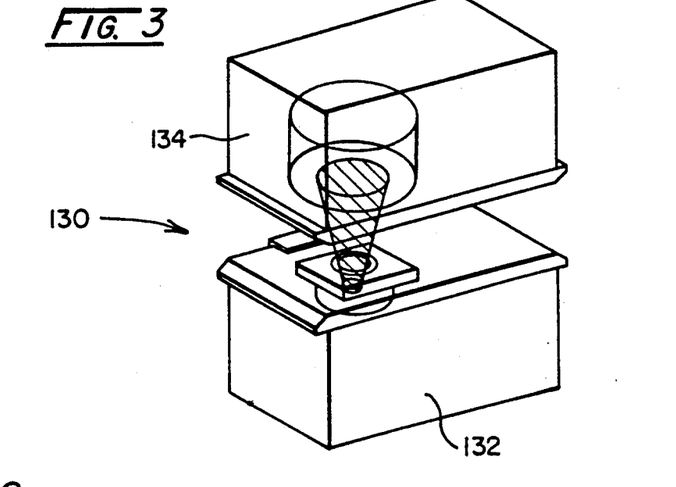
FIG. 3 is a schematic perspective view shown on an expanded scale of a basis weight sensor mounted in the gauging system platform of FIG. 2.

FIGS. 2 and 3 show a simplified nucleonic basis weight sensor 130 which can be utilized in the present invention. The sensor 130 includes a source head 132 which contains a beta emitting radioisotope such as Sr-90, Kr-85 or Pm-147, and a detector head 134 for detecting the beta particles which are transmitted through a sheet 136 of material which is to be measured by the sensor 130. The source head 132 and detector head 134 are positioned on opposite sides of the sheet 136 in fixed vertical relation to one another and moved or scanned across the sheet 136 by a stable sensor foundation or platform 138. The source head 132 includes radiation beam collimation and beam shaping components to define a beam of radiation which impinges on the lower surface of the sheet 136. The radiation beam interacts by one or more nuclear processes with the air column and the material of the sheet 136 in the gap between the heads 132, 134. A portion of the radiation beam is transmitted through the sheet 136 and enters the detector head 134. Known circuitry (not shown) associated with the detector head 134 is responsive to the total number of beta particles, and their kinetic energies, that enter an ionization chamber (not shown) in the detector head 134 and produces a corresponding output signal.

Figure 4:
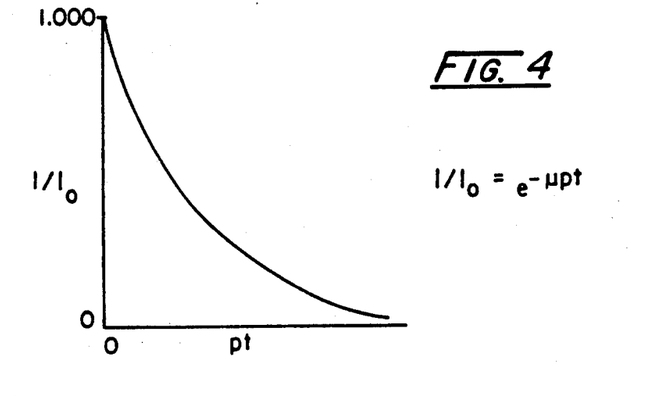
FIGS. 4 through 6 are graphs illustrating calibration characteristics or curves of the basis weight sensor of FIG. 3.

The general form of the basis weight equation which relates the radiation intensity I transmitted through the sheet 136 and detected by the detector head 134 to the radiation intensity $I_o$ detected by the detector head 134 in the total absence of the sheet 136 is shown graphically in FIG. 4 and is, $$I = I_o e^{-\mu p t} \tag{1}$$

where
- $I_o$ = radiation beam intensity detected in the absence of sheet material
- $I$ = radiation beam intensity detected in the presence of sheet material
- $\mu$ = mass attenuation coefficient
- $\rho$ = density of the material
- $t$ = thickness of the material Although $\mu$ is a complex variable, it can be modeled and if done properly, the model will remain fixed for a given nuclear source, sensor geometry, and measured process material. A number of models have been developed. One such model represents $\mu$ by the polynomial relationship, $$\mu = \mu_o = \mu_1 \ln(I/I_o) = \mu_2 \ln^2(I/I_o) = \mu_3 \ln^3(I/I_o) = ...$$

The coefficients $\mu_o, \mu_1, \mu_2, ...$ are often referred to as the sensor head constants and are obtained during a calibration procedure during which polyester samples such as those sold under the name Mylar or other suitable reference samples of different basis weights are measured in the sensor 130.

Taking the natural logarithm of both sides of equation (1) and rearranging terms results in the equation, $$\mu \rho t = \ln I - \ln I_o \quad (2)$$

Figure 5:
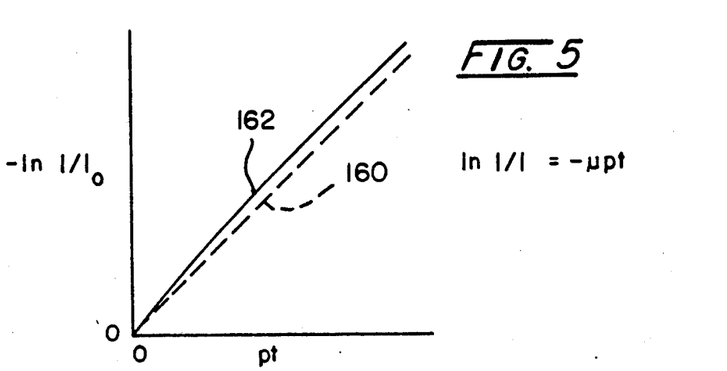
Figure 6:
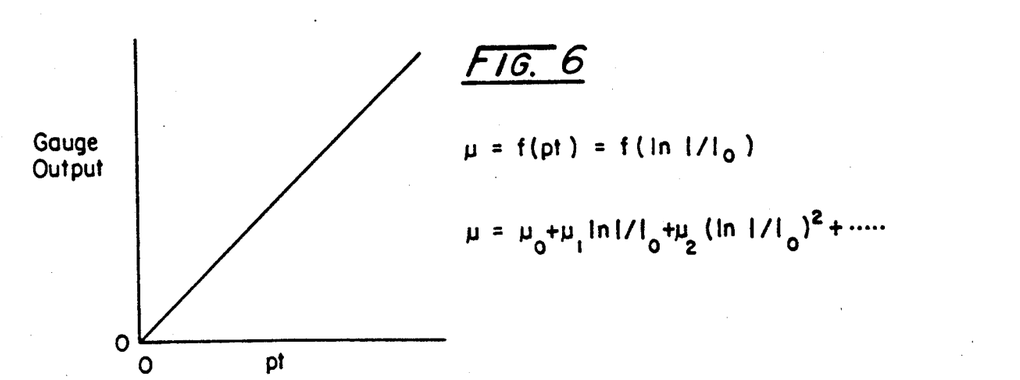

Product calibrations corresponding to sheet material to be monitored or a coating applied to such a sheet is performed by applying a linearization approximation which presumes that the ratio of $\mu_p$, the mass attenuation coefficient of the product or material to be monitored, to $\mu_m$, the mass attenuation coefficient of Mylar, is constant and results in a linear calibration curve, $$B_w = m(\mu \rho t) = b \quad (3)$$

where
- $B_w$ = the basis weight of the product
- $m$ = the product slope
- $b$ = the product offset These relationships and the resulting output from the sensor 130 are represented graphically in FIGS. 5 and 6 wherein dashed line 160 at 45° represents what one would obtain upon taking the logarithm of a truly exponential function and solid line 162 is what results upon taking the natural logarithm of equation (1). Total linearization is obtained by selection of appropriate sensor head constants to model $\mu$. This approximation is applicable to many sensing applications and if refinements are necessary, such refinements will be apparent to those skilled in the art.

A problem is encountered when two different calibrations, for example one calibration corresponding to the base substrate 102 and one calibration intended to represent the desired combination of the base substrate 102 and the adhesive layer 112, are used for basis weight ($B_w$) sensors positioned on opposite sides of a coating station. For such calibrations, the result obtained by subtracting the $B_w$ signal generated by the sensor preceding the station from the $B_w$ signal generated by the sensor succeeding the station does not consistently yield the $B_w$ of the coating material applied by the station. This problem or measurement error is due to variations in the composition of the base substrate 102, particularly when recycled material is used, and varying ratios of the $B_w$ of the substrate 102 to the $B_w$ of the coating 112 due to such base substrate variations and normal operation of the system 100.

The problem is solved in accordance with the present invention by using the same product calibration which corresponds to the coating on the sensor positioned before a coating station and the sensor located after the same coating station. If the sensors are composition or material sensitive as is typically the case, the measurement of the substrate taken before the coating station will be incorrect. However, the error will be the same for both sensors such that the difference signal, expressed in coating terms, which is obtained by subtracting the signal generated by the sensor preceding the coating station from the signal generated by the sensor succeeding the coating station will accurately indicate the true $B_w$ of the coating applied by the station. Thus, in accordance with the present invention, the $B_w$ of each coating applied by an industrial coating process can be measured and/or controlled.

If the correct substrate $B_w$ is required, it can be obtained from the sensor preceding the coating station by multiplying the measured value by the ratio of the substrate product calibration to the coating product calibration. Alternately, the sensor preceding the coating station can be calibrated with the product calibration corresponding to the substrate to directly read the substrate $B_w$. Since many available $B_w$ sensors permit multiple product calibrations to be entered into each sensor and can simultaneously generate a corresponding number of output signals, measuring the $B_w$ of a base substrate, a finished product, a plurality of coatings and intermediate products comprising the base substrate and one or more layers of material coated onto the substrate can be easily performed.

Returning to FIG. 1, in the industrial system 100 the $B_w$ of the coating applied by the first coating station 104 is determined by calibrating the first and second gauging means or $B_w$ sensors 120, 122 with a product calibration corresponding to the first layer, i.e. the adhesive layer 112. Calculating means comprising a control console 150 provides for determining the basis weight of the adhesive coating 112 by subtracting the first output signal generated by the first gauging system or $B_w$ sensor 120 from the second output signal generated by the second gauging system or $B_w$ sensor 122. The control console 150 normally also comprises process control means for controlling at least one of the characteristics of the multilayer product, in this case the $B_w$ of the first or adhesive layer 112. The process control means generates process control signals from the determined basis weight of the first and any other layers of a multilayer product to control the first processing station and any other processing stations by means of control signals which are carried to the coating stations 104, 106, 108 via conductors 152.

The industrial system 100 when configured to produce sandpaper further comprises third gauging means comprising the third $B_w$ sensor 124 which is positioned on the output side 106B of a second processing station or second coating station 106 which applies the second or grit layer 116 onto the adhesive layer 112 to form the final multilayer product 118, or sandpaper. The third $B_w$ sensor 124 monitors the combination of the base substrate 102, the first or adhesive layer 112 applied by the first coating station 104 and the second or grit layer 116 applied by the second coating station 106. The second and third $B_w$ sensors 122 and 124 are calibrated with a product calibration corresponding to the second or grit layer 116, and the calculating means or control console 150 further provides for determining the $B_w$ of the grit layer 116 by subtracting a third output signal generated by the second $B_w$ sensor 122 and corresponding to the product calibration for the grit layer 116 from a fourth output signal generated by the third $B_w$ sensor 124. In this way, the first or adhesive layer 112 and the second or grit layer 116 can be measured and/or controlled. The $B_w$ of the base substrate 102, the $B_w$ of the intermediate product 114 and the $B_w$ of the final multilayer product 118 can be determined by taking ratios of the corresponding product calibrations and applying the ratios to output signals from the appropriate $B_w$ sensors as previously described. Alternately, the $B_w$ sensors could be calibrated with the appropriate product calibrations to directly read these $B_w$'s.

In accordance with broad apparatus aspects of the present invention, a system for measuring characteristics of a product including a base substrate and at least one layer of material deposited, coated or otherwise applied to said base substrate as it passes through a number of processing stations corresponding to at least the number of layers to be measured may comprise a plurality of gauging means or $B_w$ sensors 122-128 positioned on input and output sides of the processing or coating stations 104-108. Each $B_w$ sensor 122-128 includes calibration means for defining a plurality of product calibrations each corresponding to one material or a combination of materials to be monitored, such as the base substrate 102 and one or more layers 112, 116 applied thereto, and being calibrated with product calibrations corresponding to the product or intermediate stage of the product monitored by the $B_w$ sensor, the layer applied by the processing station preceding the $B_w$ sensor, if any, and the layer applied by the processing station succeeding the $B_w$ sensor, if any. Finally, calculating means comprising the control console 150 or incorporated into the control console 150 are provided for determining the $B_w$ of the resulting product and/or one or more intermediate stages of the resulting product from output signals generated by the corresponding $B_w$ sensors based on the product calibrations corresponding to the resulting product and each intermediate stage of the resulting product, and determining the basis weight of each layer of material of the resulting product by subtracting an output signal generated by the $B_w$ sensor preceding the processing station applying the layer based on the product calibration corresponding to that layer from an output signal generated by the $B_w$ sensor succeeding the processing station applying that layer based on the product calibration corresponding to the layer.

In accordance with broad method aspects of the present invention for use in an industrial process wherein a base substrate passes through a number of processing stations for depositing, coating or otherwise applying one or more layers of material to the base substrate wherein gauging systems are positioned on input and output sides of the processing stations and include calibration means for defining a plurality of product calibrations each corresponding to one material or a combination of materials to be monitored, such as the base substrate and one or more layers applied thereto, a method for measuring characteristics of a resulting product and intermediate stages of the resulting product comprises the steps of: calibrating each of the gauging systems with product calibrations corresponding to the product or intermediate product monitored by the gauging system, the layer applied by the processing station preceding the gauging system, if any, and the layer applied by the processing station succeeding the gauging system, if any; determining the basis weight of the resulting product and each intermediate stage of the resulting product from output signals generated by the corresponding gauging systems based on the product calibrations corresponding to the resulting product and each intermediate stage of the resulting product; and, determining the basis weight of each layer of material of the resulting product by subtracting an output signal generated by the gauging system preceding the processing station applying the layer based on the product calibration corresponding to the layer from an output signal generated by the gauging system succeeding the processing station applying the layer based on the product calibration corresponding to the layer.

Having thus described the method and apparatus for measuring characteristics of a multilayer product of the present invention in detail and by reference to preferred embodiments thereof, it will be apparent that modifications and variations are possible without departing from the scope of the invention defined in the appended claims.

What is claimed is:

1. A method for measuring characteristics of a product including a substrate and at least one layer of material different than the substrate deposited, coated or otherwise applied thereto as the substrate passes through a number of processing stations corresponding to at least the number of layers to be measured, the method comprising the steps of:

positioning a first gauging system on an input side of a first processing station to monitor a base substrate prior to entering said first processing station;

positioning a second gauging system on an output side of said first processing station to monitor said base substrate and a first layer applied by said first processing station;

calibrating said first and second gauging systems with a product calibration corresponding to said first layer; and determining the basis weight of said first layer by subtracting a first output signal generated by said first gauging system from a second output signal generated by said second gauging system.

2. A method for measuring characteristics of a product as claimed in claim 1 and further providing for controlling at least one of said characteristics comprising the step of generating a process control signal from the determined basis weight of said first layer to control said first processing station.

3. A method for measuring characteristics of a product as claimed in claim 1 further comprising the steps of:

taking a ratio of a product calibration corresponding to the substrate to the product calibration corresponding to said first layer; and determining the basis weight of the substrate by multiplying said first output signal by said ratio.

4. A method for measuring characteristics of a product as claimed in claim 1 further comprising the steps of:

positioning a third gauging system on an output side of a second processing station to monitor said base substrate, said first layer applied by said first processing station and a second layer applied by said second processing station;

calibrating said second and third gauging systems with a product calibration corresponding to said second layer; and determining the basis weight of said second layer by subtracting a third output signal generated by said second gauging system and corresponding to the product calibration for said second layer from a fourth output signal generated by said third gauging system.

5. A method for measuring characteristics of a product as claimed in claim 4 and further providing for controlling at least one of said characteristics comprising the step of generating a process control signal from the determined basis weight of said first layer to control said first processing station.

6. A method for measuring characteristics of a product as claimed in claim 4 further comprising the steps of:

taking a ratio of a product calibration corresponding to the combination of said base substrate and said first layer to the product calibration corresponding to said second layer; and determining the basis weight of the combination of said base substrate and said first layer by multiplying said third output signal by said ratio.

7. A method for measuring characteristics of a product including a substrate and at least one layer of material different than the substrate deposited, coated or otherwise applied thereto as the substrate passes through a number of processing stations corresponding to at least the number of layers to be measured, the method comprising the steps of:

positioning a first gauging system on an input side of a first processing station to monitor a base substrate prior to entering said first processing station, said first gauging system including calibration means for defining a plurality of product calibrations each corresponding to one of the following: said substrate, a material to be applied by an appropriate process to said substrate, or a combination of materials comprising said base substrate and one or more layers applied thereto;

positioning a second gauging system on an output side of said first processing station to monitor said base substrate and a first layer applied by said first processing station, said second gauging system including calibration means for defining a plurality of product calibrations each corresponding to one of the following: said substrate, a material to be applied by an appropriate process to said substrate, or a combination of materials comprising said base substrate and one or more layers applied thereto;

calibrating said first gauging system with product calibrations corresponding to said base substrate and said first layer;

calibrating said second gauging system with product calibrations corresponding to said first layer and to the combination of said base substrate and said first layer;

determining the basis weight of said base substrate from an output signal generated by said first gauging system based on the product calibration corresponding to said base substrate;

determining the basis weight of said first coating by subtracting an output signal generated by said first gauging system based on the product calibration corresponding to said first layer from an output signal generated by said second gauging system based on the product calibration corresponding to said first layer; and determining the basis weight of the combination of said base substrate and said first layer from an output signal generated by said second gauging system based on the product calibration corresponding to the combination of said base substrate and said first layer.

8. A method for measuring characteristics of a product including a substrate and at least one layer of material different than the substrate deposited, coated or otherwise applied to the substrate as claimed in claim 7 further comprising the steps of:

positioning a third gauging system on an output side of a second processing station to monitor the combination of said base substrate, said first layer and a second layer applied to the combination of said base substrate and said first layer by said second processing station, said third gauging system including calibration means for defining a plurality of product calibrations each corresponding to one of the following: said substrate, a material to be applied by an appropriate process to said substrate, or a combination of materials comprising said base substrate and one or more layers applied thereto;

further calibrating said second gauging system with a product calibration corresponding to said second layer;

calibrating said third gauging system with product calibrations corresponding to said second layer and to the combination of said base substrate and said first and second layers;

determining the basis weight of said second coating by subtracting an output signal generated by said second gauging system based on the product calibration corresponding to said second layer from an output signal generated by said third gauging system based on the product calibration corresponding to said second layer; and determining the basis weight of the combination of said base substrate and said first and second layers from an output signal generated by said third gauging system based on the product calibration corresponding to the combination of said base substrate and said first and second layers.

9. In an industrial process wherein a base substrate passes through a number of processing stations for depositing, coating or otherwise applying one or more layers of material different than said base substrate thereto wherein gauging systems are positioned on input and output sides of said processing stations and include calibration means for defining a plurality of product calibrations each corresponding to one of the following: said substrate, a material to be applied by an appropriate process to said substrate, or a combination of materials comprising said base substrate and one or more layers applied thereto, a method for measuring characteristics of a resulting product and intermediate stages of said resulting product comprising the steps of:

calibrating each of said gauging systems with product calibrations corresponding to the product or intermediate product monitored by said gauging system, the layer applied by the processing station preceding said gauging system, if any, and the layer applied by the processing station succeeding said gauging system, if any;

determining the basis weight of said resulting product and each intermediate stage of said resulting product from output signals generated by the corresponding gauging systems based on the product calibrations corresponding to said resulting product and each intermediate stage of said resulting product; and determining the basis weight of each layer of material of said resulting product by subtracting an output signal generated by the gauging system preceding the processing station applying said layer based on the product calibration corresponding to said layer from an output signal generated by the gauging system succeeding the processing station applying said layer based on the product calibration corresponding to said layer.

10. A system for measuring characteristics of a product including a substrate and at least one layer of material different than the substrate deposited, coated or otherwise applied thereto as the substrate passes through a number of processing stations corresponding to at least the number of layers to be measured, said system comprising:

first gauging means positioned on an input side of a first processing station for monitoring a base substrate prior to entering said first processing station and generating a first output signal representative of said base substrate;

second gauging means positioned on an output side of said first processing station for monitoring said base substrate and a first layer applied by said first processing station and generating a second output signal representative of said substrate and said first layer, said first and second gauging means being calibrated with a product calibration corresponding to said first layer; and calculating means for determining the basis weight of said first layer by subtracting the first output signal generated by said first gauging system from the second output signal generated by said second gauging system.

11. A system for measuring characteristics of a product as claimed in claim 10 further comprising process control means for controlling at least one of said characteristics, said process control means generating a process control signal from the determined basis weight of said first layer to control said first processing station.

12. A system for measuring characteristics of a product as claimed in claim 10 wherein said control means further provides for taking a ratio of a product calibration corresponding to the substrate to the product calibration corresponding to said first layer and determining the basis weight of said base substrate by multiplying said first output signal by said ratio.

13. A system for measuring characteristics of a product as claimed in claim 10 further comprising:

third gauging means positioned on an output side of a second processing station for monitoring the combination of said base substrate, said first layer applied by said first processing station and a second layer applied by said second processing station, said second and third gauging means being calibrated with a product calibration corresponding to said second layer; and said calculating means further providing for determining the basis weight of said second layer by subtracting a third output signal generated by said second gauging system and corresponding to the product calibration of said second layer from a fourth output signal generated by said third gauging system.

14. A system for measuring characteristics of a product including a substrate and at least one layer of material different than the substrate deposited, coated or otherwise applied thereto as the substrate passes through a number of processing stations corresponding to at least the number of layers to be measured, said system comprising:

first gauging means positioned on an input side of a first processing station for monitoring a base substrate prior to entering said first processing station, said first gauging means including calibration means for defining a plurality of product calibrations each corresponding to said substrate, a material to be deposited, coated or otherwise applied to said substrate, or a combination of materials to be monitored comprising said base substrate and one or more layers applied thereto, said first gauging means being calibrated with product calibrations corresponding to said base substrate and said first layer;

second gauging means positioned on an output side of said first processing station for monitoring said base substrate and a first layer applied by said first processing station, said second gauging means including calibration means for defining a plurality of product calibrations each corresponding to said substrate, a material to be deposited, coated or otherwise applied to said substrate, or a combination of materials to be monitored comprising said base substrate and one or more layers applied thereto, said second gauging means being calibrated with product calibrations corresponding to said first layer and to the combination of said base substrate and said first layer; and calculating means for determining the basis weight of said base substrate form an output signal generated by said first gauging system based on the product calibration corresponding to said base substrate, the basis weight of said first layer by subtracting an output signal generated by said first gauging system base on the product calibration corresponding to said first layer from an output signal generated by said second gauging system based on the product calibration corresponding to said first layer, and the basis weight of the combination of said base substrate and said first layer from an output signal generated by said second gauging system based on the product calibration corresponding to the combination of said base substrate and said first layer.

15. A system for measuring characteristics of a product including a base substrate and at least one layer of material different than said base substrate deposited, coated or otherwise applied to said base substrate as it passes through a number of processing stations corresponding to at least the number of layers to be measured, said system comprising:

a plurality of gauging means positioned on input and output sides of the processing stations each including calibration means for defining a plurality of product calibrations each corresponding to one of the following: said substrate, a material to be applied by an appropriate process to said substrate, or a combination of materials comprising said base substrate and one or more layers applied thereto, said plurality of gauging means each being calibrated with product calibrations corresponding to the product or intermediate stage of the product monitored by said gauging system, the layer applied by the processing station preceding said gauging means, if any, and the layer applied by the processing station succeeding said gauging system, if any; and calculating means for determining the basis weight of the product or any one or more of the intermediate stages of the product from output signals generated by the corresponding gauging means based on the product calibrations corresponding to the product and each intermediate stage of the product, and determining the basis weight of each layer of material of the product by subtracting an output signal generated by the gauging system preceding the processing station applying said layer based on the product calibration corresponding to said layer from an output signal generated by the gauging system succeeding the processing station applying said layer based on the product calibration corresponding to said layer.

* * * * *

UNITED STATES PATENT AND TRADEMARK OFFICE
CERTIFICATE OF CORRECTION

PATENT NO. : 5,020,356

DATED : June 4, 1991

INVENTOR(S) : John R. Dukes

It is certified that error appears in the above-identified patent and that said Letters Patent is hereby corrected as shown below:

Col. 3, Line 66, "apPlied" should be --applied--

Col. 9, Line 16, "$\mu=\mu_0=\mu_1\ln(I/I_0)=\mu_2\ln^2(I/I_0)=\mu_3\ln3(I/I_0)=...$"

should be $--\mu=\mu_0+\mu_1\ln(I/I_0)+\mu_2\ln^2(I/I_0)+\mu_3\ln3(I/I_0)+...--$ Col. 9, Line 37, "$B_w=m(\mu pt)=b$" should be --$B_w=m(\mu pt)+b$--

Col. 15, Line 68, "of" should be --for--

Col. 16, Line 38, "form" should be --from--

Signed and Sealed this

Ninth Day of February, 1993

*Attest:*

STEPHEN G. KUNIN

*Attesting Officer*     *Acting Commissioner of Patents and Trademarks*